(12) United States Patent
Chhatbar et al.

(10) Patent No.: US 10,052,361 B2
(45) Date of Patent: Aug. 21, 2018

(54) LIQUID PHARMACEUTICAL COMPOSITION OF CONJUGATED ERYTHROPOIETIN

(71) Applicant: INTAS PHARMACEUTICALS LTD., Ahmedabad (IN)

(72) Inventors: Chandresh Chhatbar, Sanand Ahmedabad (IN); Vijaykant Pandey, Sanand Ahmedabad (IN); Nildip Chauhan, Sanand Ahmedabad (IN)

(73) Assignee: INTAS PHARMACEUTICALS LTD, Ahmedabad (IN)

( * ) Notice: Subject to any disclaimer, the term of this patent is extended or adjusted under 35 U.S.C. 154(b) by 0 days.

(21) Appl. No.: 15/300,504

(22) PCT Filed: Feb. 27, 2015

(86) PCT No.: PCT/IB2015/051462
§ 371 (c)(1),
(2) Date: Sep. 29, 2016

(87) PCT Pub. No.: WO2015/150930
PCT Pub. Date: Oct. 8, 2015

(65) Prior Publication Data
US 2017/0112901 A1    Apr. 27, 2017

(30) Foreign Application Priority Data
Mar. 29, 2014 (IN) .......................... 1366/MUM/2014

(51) Int. Cl.
| C07K 14/505 | (2006.01) |
| C07K 1/107  | (2006.01) |
| A61K 38/18  | (2006.01) |
| A61K 47/48  | (2006.01) |
| A61K 47/02  | (2006.01) |
| A61K 47/12  | (2006.01) |
| A61K 47/18  | (2017.01) |
| A61K 47/26  | (2006.01) |

(52) U.S. Cl.
CPC .......... *A61K 38/1816* (2013.01); *A61K 47/02* (2013.01); *A61K 47/12* (2013.01); *A61K 47/183* (2013.01); *A61K 47/26* (2013.01); *A61K 47/48215* (2013.01); *C07K 1/107* (2013.01); *C07K 14/505* (2013.01)

(58) Field of Classification Search
None
See application file for complete search history.

(56) References Cited

U.S. PATENT DOCUMENTS

| 4,992,419 | A  |  2/1991 | Woog et al. |
| 6,120,761 | A  |  9/2000 | Yamazaki et al. |
| 7,011,825 | B2 |  3/2006 | Yamazaki et al. |
| 7,202,208 | B2 |  4/2007 | Papadimitriou |
| 2005/0119172 | A1* | 6/2005 | Merkle ................ C07K 14/76 424/184.1 |
| 2006/0029551 | A1 | 2/2006 | Liu et al. |
| 2006/0287224 | A1* | 12/2006 | DeFrees ............. A61K 38/1816 514/7.7 |

FOREIGN PATENT DOCUMENTS

| IN | 220067 | 5/2008 |
| IN | 234438 | 5/2009 |

OTHER PUBLICATIONS

International Search Report for PCT/IB2015/051462, Completed by the Indian Patent Office dated May 29, 2015, 3 Pages.
European Extended Search Report dated Oct. 10, 2017 for EP Appn. No. 15772815.5, 10 pgs.

* cited by examiner

*Primary Examiner* — Elizabeth C. Kemmerer
*Assistant Examiner* — Regina M DeBerry
(74) *Attorney, Agent, or Firm* — Brooks Kushman P.C.

(57) ABSTRACT

A liquid pharmaceutical composition having a conjugated erythropoietin, buffer, sugar, tonicity modifier and amino acid as an aggregation inhibitor. The liquid pharmaceutical composition provides a stable pharmaceutical composition which encompasses conjugated erythropoietin, acetate buffer, sucrose, arginine and sodium chloride which is maintained at a pH of about 4.9 to 5.3.

2 Claims, 10 Drawing Sheets

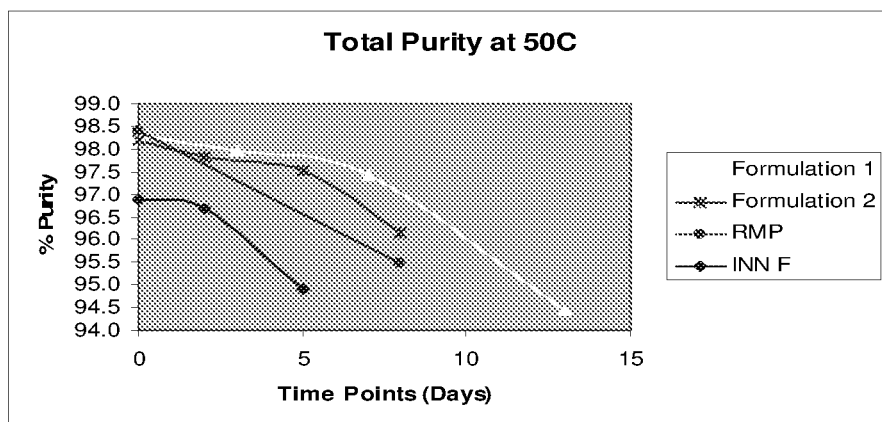
Figure 1: Graph of Purity by SE HPLC

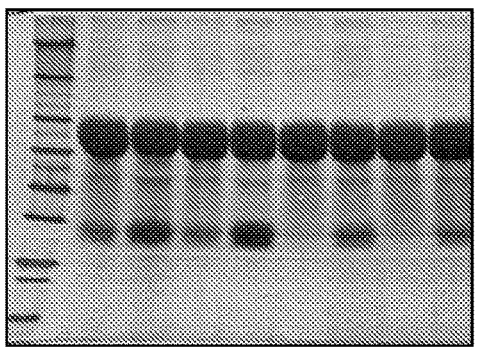

| 1 | Marker |
|---|---|
| 2 | Histidine -Hcl buffer, 2-8 °C |
| 3 | Histidine -Hcl buffer, 40 °C |
| 4 | Histidine-acetate buffer, 2-8 °C |
| 5 | Histidine-acetate buffer, 40 °C |
| 6 | Arginine-acetate buffer, 2-8 °C |
| 7 | Arginine-acetate buffer, 40 °C |
| 8 | Succinate buffer, 2-8 °C |
| 9 | Succinate buffer, 40 °C |

Figure 2: Non-reducing gel

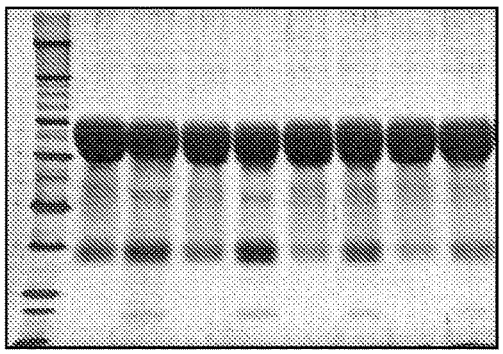

| 1 | Marker |
|---|---|
| 2 | Histidine -Hcl buffer, 2-8 °C |
| 3 | Histidine -Hcl buffer, 40 °C |
| 4 | Histidine-acetate buffer, 2-8 °C |
| 5 | Histidine-acetate buffer, 40 °C |
| 6 | Arginine-acetate buffer, 2-8 °C |
| 7 | Arginine-acetate buffer, 40 °C |
| 8 | Succinate buffer, 2-8 °C |
| 9 | Succinate buffer, 40 °C |

Figure 3: Reducing gel

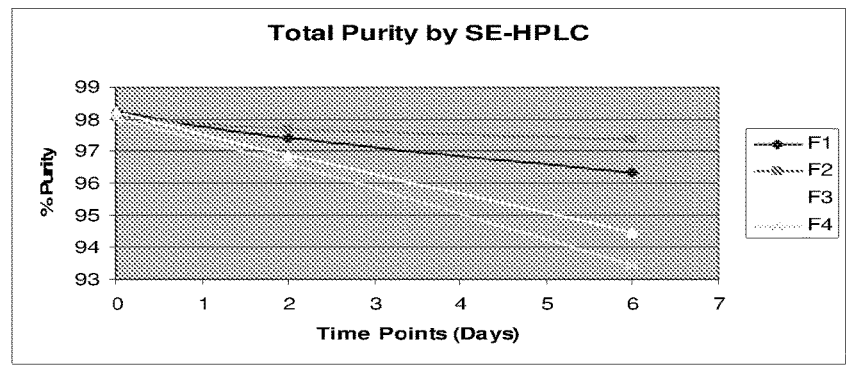
Figure 4: Graph of Purity by SE HPLC
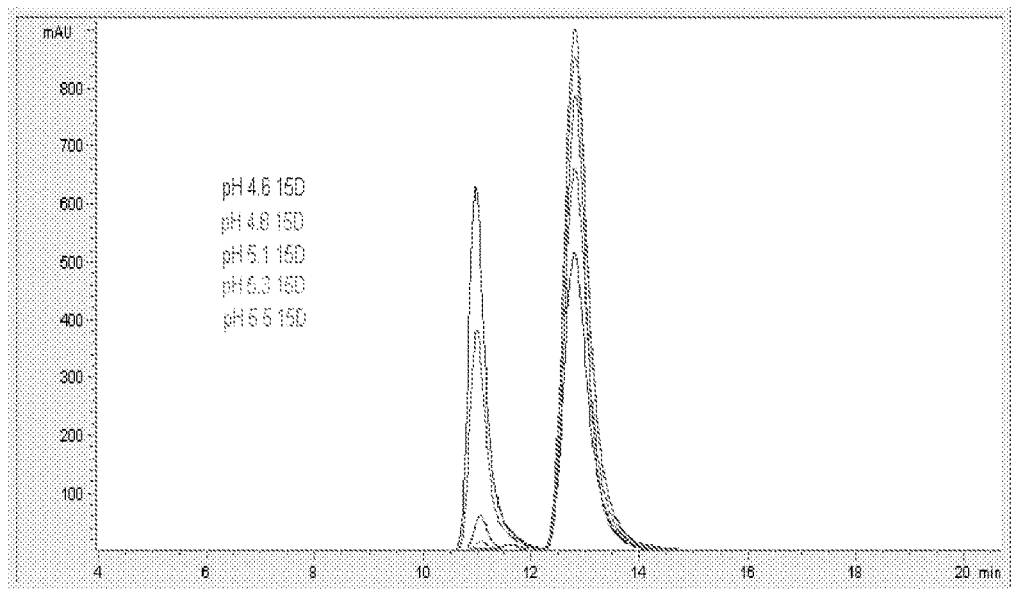
Figure 5: SEC HPLC chromatogram of the 15 D pH study

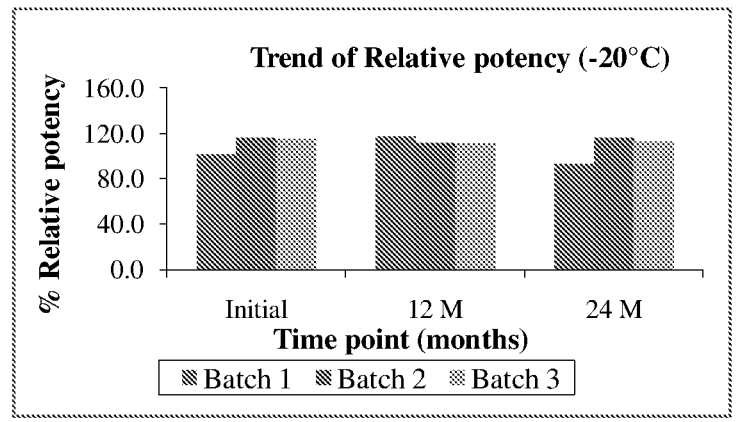
Figure 6 : Trend for % relative potency of Pegylated Erythropoietin (1.6 mg/mL in PETG bottle) charged at -20 °C
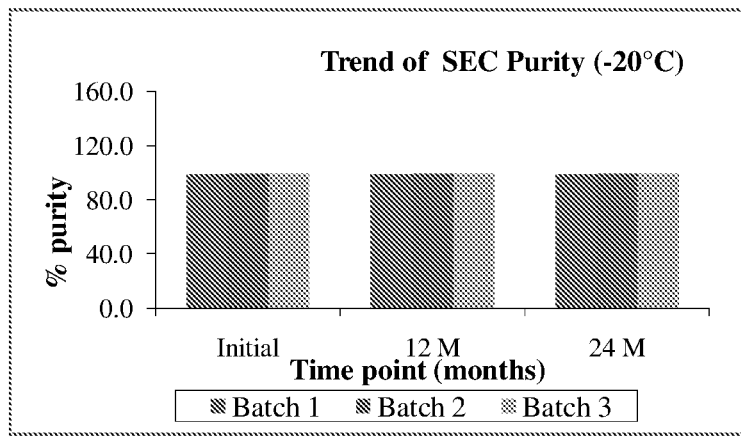
Figure 7 : Trend for % purity by SE-HPLC of Pegylated Erythropoietin (1.6 mg/mL in PETG bottle) charged at -20 °C

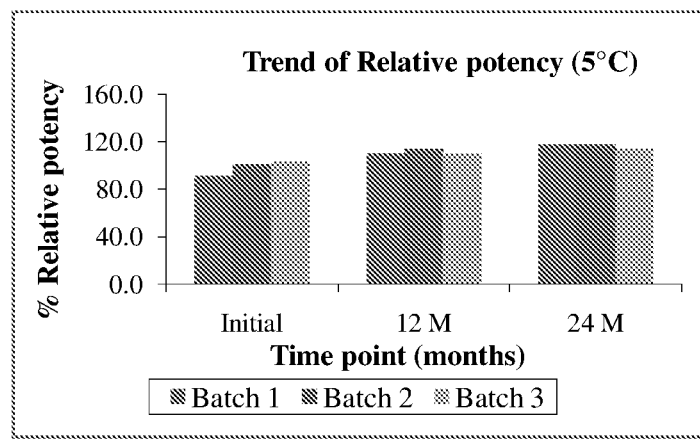
Figure 8 : Trend for % relative potency of Pegylated Erythropoietin (1.33 mg/mL in 1 mL USP type-I glass syringe barrel) charged at 5 °C
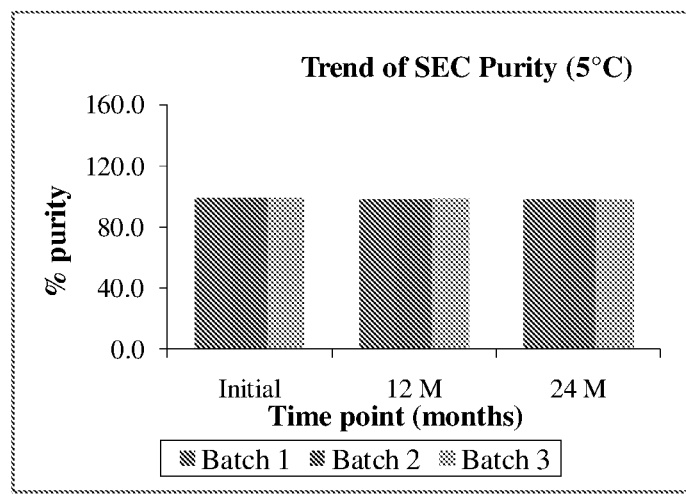
Figure 9 : Trend for % purity by SE-HPLC of Pegylated Erythropoietin (1.33 mg/mL in 1 mL USP type-I glass syringe barrel) charged at 5 °C

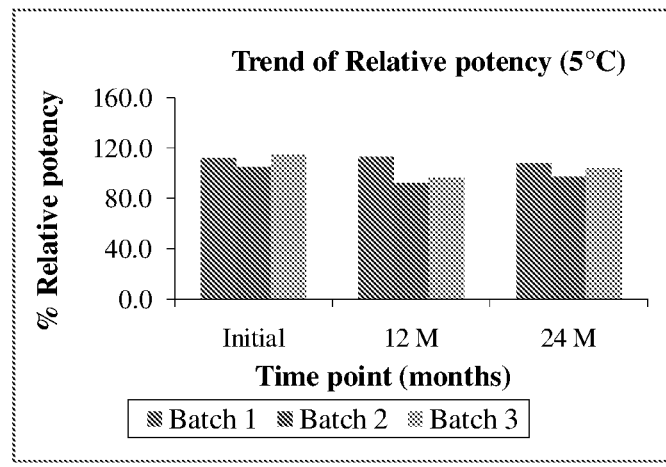
Figure 10 : Trend for % relative potency of Pegylated Erythropoietin (0.17 mg/mL in 1 mL USP type-I glass syringe barrel) charged at 5 °C
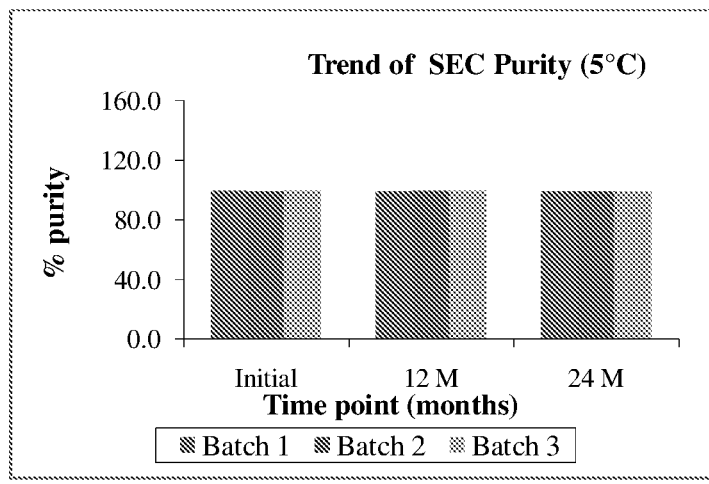
Figure 11 : Trend for % purity by SE-HPLC of Pegylated Erythropoietin (0.17 mg/mL in 1 mL USP type-I glass syringe barrel) charged at 5 °C

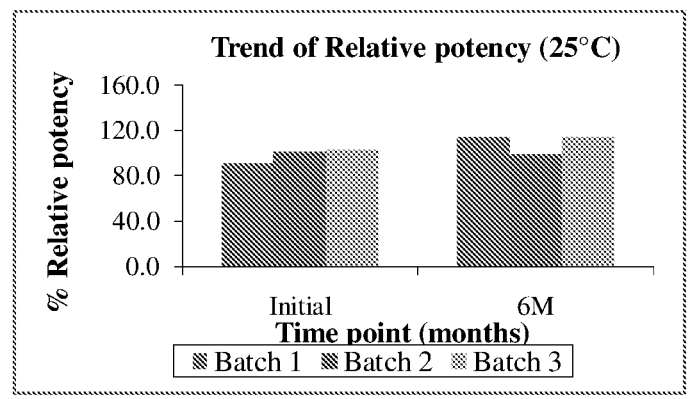
Figure 12 : Trend for % relative potency of Pegylated Erythropoietin (1.33 mg/mL in 1 mL USP type-I glass syringe barrel) charged at 25 °C
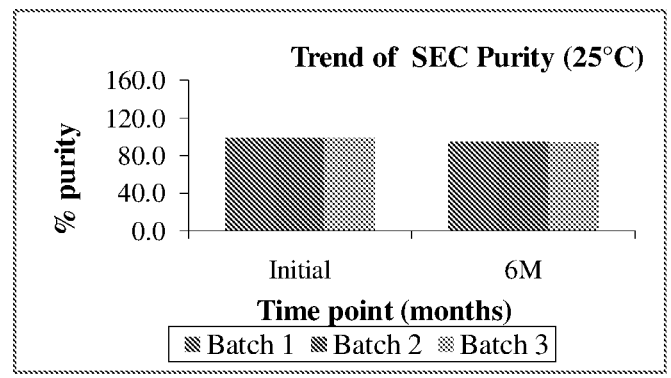
Figure 13 : Trend for % purity by SE-HPLC of Pegylated Erythropoietin (1.33 mg/mL in 1 mL USP type-I glass syringe barrel) charged at 25 °C

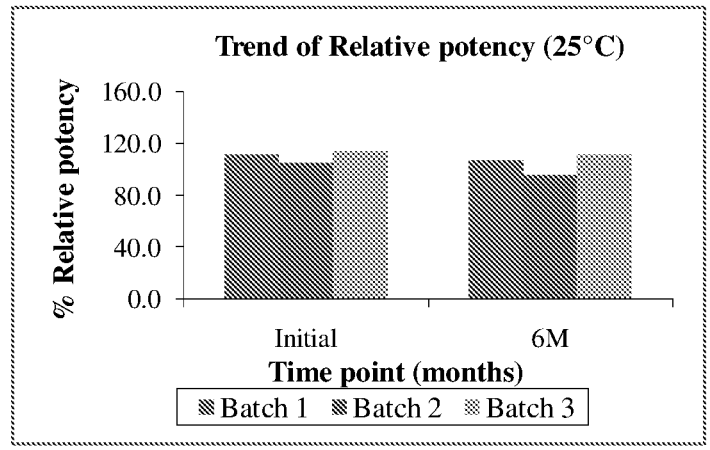
Figure 14 : Trend for % relative potency of Pegylated Erythropoietin (0.17 mg/mL in 1 mL USP type-I glass syringe barrel) charged at 25 °C
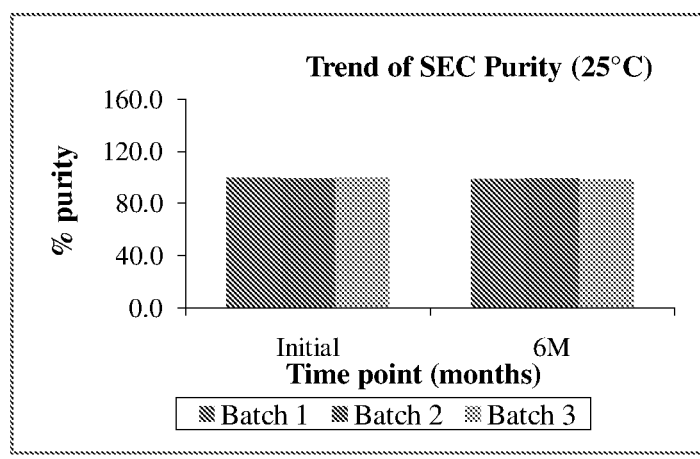
Figure 15 : Trend for % purity by SE-HPLC of Pegylated Erythropoietin (0.17 mg/mL in 1 mL USP type-I glass syringe barrel) charged at 25 °C

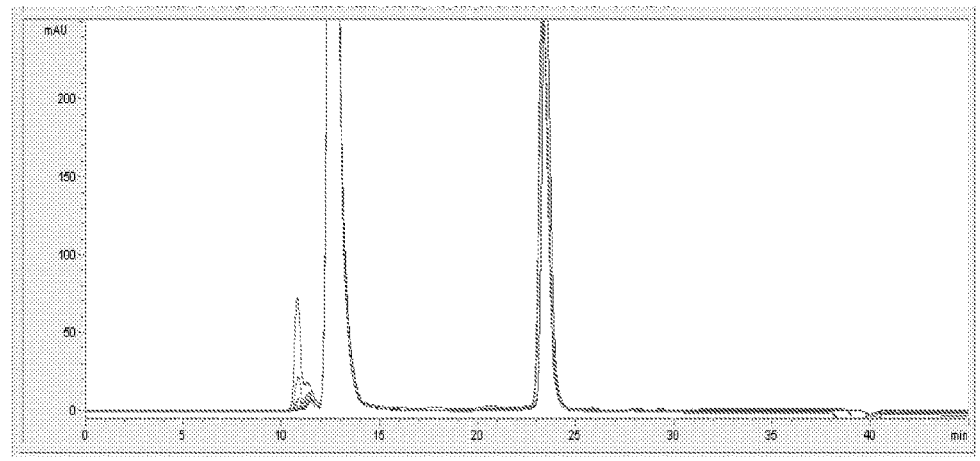
Figure 16: overlay of chromatogram of SEC HPLC
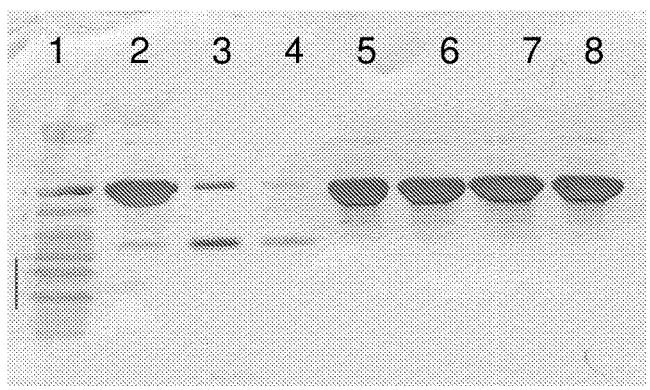
| Western Blot | |
|---|---|
| Lane | Sample |
| 1 | Preatained marker |
| 2 | RMP |
| 3 | 2% EPO + RMP |
| 4 | 1% EPO + RMP |
| 5 | IPL formulation Zero day |
| 6 | IPL formulation Zero day |
| 7 | IPL formulation Zero day |
| 8 | IPL formulation Zero day |
Figure 17: Western Blot result at Zero day

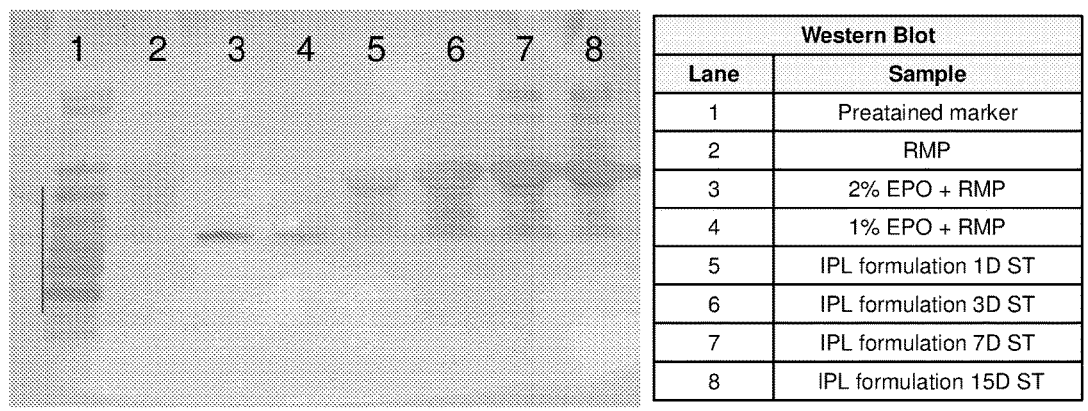
Figure 18: Western blot result at 1D, 3D, 7D & 15D
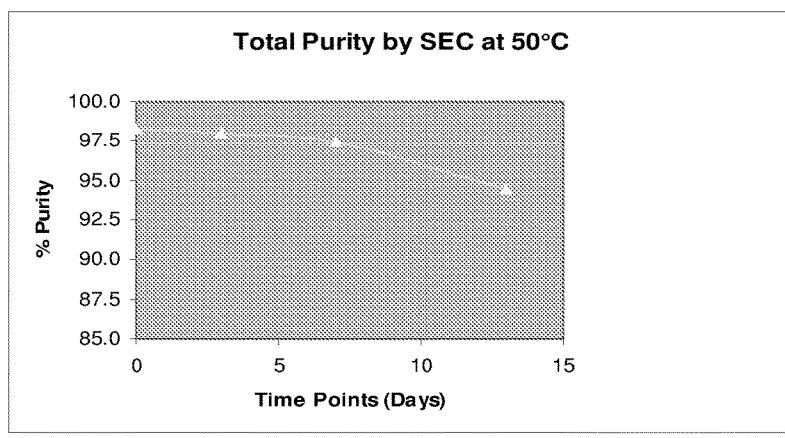
Figure 19: Graph of purity by SEC HPLC

LIQUID PHARMACEUTICAL COMPOSITION OF CONJUGATED ERYTHROPOIETIN

CROSS-REFERENCE TO RELATED APPLICATION

This application is the U.S. national phase of PCT Application No. PCT/IB2015/051462 filed on Feb. 27, 2015, which claims priority to IN Patent Application No. 1366/mum/2014 filed on Mar. 29, 2014, the disclosures of which are incorporated in their entirety by reference herein.

RELATED APPLICATION

This application is related to Indian Provisional Application 1366/MUM/2014 filed 29Mar. 2014 and is incorporated herein in its entirety.

FIELD OF THE INVENTION

The present invention relates to a liquid pharmaceutical composition comprising a conjugated erythropoietin, buffer, sugar, tonicity modifier and amino acid as an aggregation inhibitor.

BACKGROUND OF THE INVENTION

Erythropoietin (EPO) is a glycoprotein hormone which stimulates red blood cells by a process known as erythropoiesis. EPO is produced in the kidney and stimulates the division and differentiation of committed erythroid progenitors in the bone marrow. In patients with renal insufficiency, serum EPO levels remain low, inappropriately low serum EPO levels may also be seen in anemic patients with cancer, Human Immunodeficiency Virus (HIV) infection, ulcerative colitis and sickle cell anemia. For all these indications and to decrease the rate of blood transfusion, EPO is established as an effective treatment.

The rHu EPO is a 165 amino acid containing glycoprotein produced through recombinant DNA technology in animal cell lines such as Chinese Hamster Ovary (CHO) and Baby Hamster Kidney (BHK) cell lines. The recombinant human erythropoietin (rHu EPO) has the same biological properties as endogenous erythropoietin secreted in humans. It has a molecular weight of about 36,000 daltons with carbohydrate moiety composing about 30% of molecular weight.

Pegylation technology has emerged as a means to improve the pharmacokinetic and pharmcodynamic properties of biopharmaceuticals. Some of the benefits of pegylation include improved clinical properties, enhanced solubility, sustained absorption and release, reduced immunogenicity and proteolysis, reduced clearance from circulation by the kidneys, increased dosing intervals due to higher in-vivo half-lives owing to increased circulation time and the like. The longer circulation of Erythropoietin results in beneficial therapeutic effects such as prolongation of its presence in the human body, effective therapeutic treatment of disease and conditions thereof.

Pegylated Erythropoietin (MIRCERA® from Roche) is a Pegylated recombinant form of human EPO. The erythropoietin used to generate MIRCERA® is the active substance of Neorecormon® (epoetin beta; Roche's recombinant EPO first approved for general medical use in the EU in 1996). The PEG moiety used is methoxypolyethylene glycol-succinimidyl butanoic acid (PEG-SBA); a 30 kDa linear chemically activated PEG. The PEG-SBA spontaneously forms amide linkages with either EPO's N-terminal amino group or with the E-amino group of an accessible surface lysine residue (Lys 45 or Lys 52). The final product generated is a 60 kDa monopegylated product.

U.S. Pat. No. 4,992,419 disclosed a compatible, storage-stable human protein preparation containing a human protein, a physiologically compatible buffer and optionally complex formers, isotonicity-adjusting agents, calcium chloride and other materials usual for injection purposes which, in an injectable form, contain 5 to 50 gm/liter urea, 1 to 50 gm/liter amino acid and 0.05 to 5 gm/liter non-ionic wetting agent. A process for the production of this preparation is also disclosed.

U.S. Pat. Nos. 6,120,761 and 7,011,825 disclosed an erythropoietin solution preparation containing an amino acid as a stabilizer, and having excellent long-term storage stability.

U.S. Pat. No. 7,202,208 disclosed a liquid pharmaceutical composition consisting essentially of an erythropoietin protein, a multiple charged inorganic anion in a pharmaceutically acceptable buffer suitable to keep the solution pH in the range from about 5.5 to about 7.0, and optionally one or more pharmaceutically acceptable excipients. This composition is especially useful for the prophylaxis and treatment of diseases related to erythropoiesis.

U.S. Pat. No. 7,842,661 disclosed conjugates between erythropoietin and PEG moieties. The conjugates are linked via an intact glycosyl linking group interposed between and covalently attached to the peptide and the modifying group. The conjugates are formed from glycosylated peptides by the action of a glycosyltransferase. The glycosyltransferase ligates a modified sugar moiety onto a glycosyl residue on the peptide. Also provided are methods for preparing the conjugates, methods for treating various disease conditions with the conjugates, and pharmaceutical formulations including the conjugates.

IN220067 disclosed a new stable pharmaceutical composition of erythropoietin (EPO) that is stabilized with a combination of a poloxamer polyol and a polyhydric alcohol.

IN234438 disclosed an aqueous formulation of human erythropoietin, comprising the human erythropoietin of the kind such as herein described and the range of 100 IU/ml to 120,000 IU/ml; non-ionic surfactant of the kind such as herein described and the range of 0.0001 to 0.01% (w/v), polyhydric alcohol of the kind such as herein described and the range of 0.001 to 2% (w/v), neutral amino acid of the kind such as herein described and the range of 0.001 to 2% (w/v) and sugar alcohol of the kind such as herein described and the range of 0.1 to 1.0% (w/v) as stabilizers; isotonic reagent of the kind such as herein described and the range of 0.001 to 0.7% (w/v); and buffering reagent of the kind such as herein described and the range of 1 mM to 50 mM and the range of pH 6.0 to 7.5.

However, the bioavailability of commercially available protein therapeutics such as EPO is limited by their short plasma half-life and susceptibility to protease degradation. These shortcomings prevent them from attaining maximum clinical potency.

Despite the revolutionary progress in the large-scale manufacturing of proteins for therapeutic use, effective and convenient delivery of these agents in the body remains a major challenge due to their intrinsic physicochemical properties such as large molecular size, self association, physical and chemical instability, aggregation and adsorption. Hence, a novel formulation is required which can overcome all such instability of the formulation available in prior art.

OBJECT OF THE INVENTION

The main object of the present invention is to provide a stable pharmaceutical composition of conjugated protein along with pharmaceutically acceptable carriers.

Another object of the present invention is to provide a stable pharmaceutical composition comprising a conjugated erythropoietin, buffer, sugar, amino acid as an aggregation inhibitor and tonicity modifier at a pH range of 4.8 to 5.5.

Yet another object of the present invention is to provide a stable pharmaceutical composition of conjugated erythropoietin comprising a buffer system selected from the group consisting of acetate, succinate, histidine, arginine either alone or a combination thereof.

Yet another object of the present invention is to provide a stable pharmaceutical composition of conjugated erythropoietin comprising sugar or polyol selected from the group consisting of monosaccharide such as glucose and mannose, and the like either alone or in combination thereof, dissacharides such as sucrose, trehalose, and maltose, and the like either alone or in combination thereof, sugar alcohols such as mannitol and xylitol, and the like either alone or in combination thereof.

Yet another object of the present invention is to provide a stable pharmaceutical composition of conjugated erythropoietin comprising amino acid as an aggregation inhibitor, wherein the aggregation inhibitor is selected from the group consisting of arginine, glycine, methionine, lysine either alone or a combination thereof.

Yet another object of the present invention is to provide a stable pharmaceutical composition of conjugated erythropoietin comprising tonicity modifier which is selected from the group consisting of sodium chloride, potassium chloride, calcium chloride or a combination thereof.

Yet another object of the present invention is to provide a stable pharmaceutical composition of conjugated erythropoietin which does not comprise the use of surfactant to stabilize the protein composition.

Yet another object of the present invention is to provide a stable pharmaceutical composition of conjugated erythropoietin wherein the formulation is maintained at a pH of about 4.8 to 5.5, more preferably at pH 4.9 to 5.3, in a buffer system selected from the group consisting of acetate, succinate, histidine, arginine either alone or a combination thereof.

Yet another object of the present invention is to provide a stable pharmaceutical composition which encompasses conjugated erythropoietin comprising acetate buffer, sucrose, arginine, sodium chloride and maintained at a pH of about 4.9 to 5.3.

SUMMARY OF THE INVENTION

The main aspect of the present invention is to provide a stable pharmaceutical composition of conjugated protein along with pharmaceutically acceptable carriers.

Another aspect of the present invention is to provide a stable pharmaceutical composition comprising a conjugated erythropoietin, buffer, sugar, amino acid as an aggregation inhibitor and tonicity modifier at a pH range of 4.8 to 5.5.

Yet another aspect of the present invention is to provide a stable pharmaceutical composition of conjugated erythropoietin comprising a buffer system selected from the group consisting of acetate, succinate, histidine, arginine either alone or a combination thereof.

Yet another aspect of the present invention is to provide a stable pharmaceutical composition of conjugated erythropoietin comprising sugar or polyol selected from the group consisting of monosaccharide such as glucose and mannose, and the like either alone or in combination thereof, dissacharides such as sucrose, trehalose, and maltose, and the like either alone or in combination thereof, sugar alcohols such as mannitol and xylitol, and the like either alone or in combination thereof.

Yet another aspect of the present invention is to provide a stable pharmaceutical composition of conjugated erythropoietin comprising amino acid as an aggregation inhibitor, wherein the aggregation inhibitor is selected from the group consisting of arginine, glycine, methionine, lysine either alone or a combination thereof.

Yet another aspect of the present invention is to provide a stable pharmaceutical composition of conjugated erythropoietin comprising tonicity modifier which is selected from the group consisting of sodium chloride, potassium chloride, calcium chloride or a combination thereof.

Yet another aspect of the present invention is to provide a stable pharmaceutical composition of conjugated erythropoietin which does not comprise the use of surfactant to stabilize the protein composition.

Yet another object of the present invention is to provide a stable pharmaceutical composition of conjugated erythropoietin wherein the formulation is maintained at a pH of about 4.8 to 5.5, more preferably at pH 4.9 to 5.3, in a buffer system selected from the group consisting of acetate, succinate, histidine, arginine either alone or a combination thereof.

Yet another aspect of the present invention is to provide a stable pharmaceutical composition which encompasses conjugated erythropoietin comprising acetate buffer, sucrose, arginine and sodium chloride and maintained at a pH of about 4.9 to 5.3.

BRIEF DESCRIPTION OF THE FIGURES

FIG. 1 shows the comparative SE-HPLC profile of Peg-EPO Formulations 1, 2(Table-1), RMP & INN-F at 0 D, 5 D, 10 D & 15 D.

FIGS. 2 & 3 shows the comparative reducing & non-reducing gel profile for Peg-EPO compositions in different buffers incubated at 40° C. for 2 days.

FIG. 4 shows the comparative SE-HPLC profile of Peg-EPO Formulations 1, 2, 3 & 4 (Table-3) at 0 D to 7 D.

FIG. 5 shows SE-HPLC chromatogram of the 15 D pH study.

FIG. 6 shows percentage relative potency of Pegylated Erythropoietin (1.6 mg/mL in PETG bottle) charged at −20° C.

FIG. 7 shows percentage purity by SE-HPLC of Pegylated Erythropoietin (1.6 mg/mL in PETG bottle) charged at −20° C.

FIG. 8 shows percentage relative potency of Pegylated Erythropoietin (1.33 mg/mL in 1 mL USP type-I glass syringe barrel) charged at 5° C.

FIG. 9 shows percentage purity by SE-HPLC of Pegylated Erythropoietin (1.33 mg/mL in 1 mL USP type-I glass syringe barrel) charged at 5° C.

FIG. 10 shows percentage relative potency of Pegylated Erythropoietin (0.17 mg/mL in 1 mL USP type-I glass syringe barrel) charged at 5° C.

FIG. 11 shows percentage purity by SE-HPLC of Pegylated Erythropoietin (0.17 mg/mL in 1 mL USP type-I glass syringe barrel) charged at 5° C.

FIG. 12 shows percentage relative potency of Pegylated Erythropoietin (1.33 mg/mL in 1 mL USP type-I glass syringe barrel) charged at 25° C.

FIG. 13 shows percentage purity by SE-HPLC of Pegylated Erythropoietin (1.33 mg/mL in 1 mL USP type-I glass syringe barrel) charged at 25° C.

FIG. 14 shows percentage relative potency of Pegylated Erythropoietin (0.17 mg/mL in 1 mL USP type-I glass syringe barrel) charged at 25° C.

FIG. 15 shows percentage purity by SE-HPLC of Pegylated Erythropoietin (0.17 mg/mL in 1 mL USP type-I glass syringe barrel) charged at 25° C.

FIG. 16 shows overlay of SE-HPLC chromatogram of conjugated erythropoietin composition FIG. 17 shows western blot analysis at 0 D.

FIG. 18 shows western blot analysis at 1 D, 3 D, 7 D & 15 D.

FIG. 19 shows purity analysis of conjugated erythropoietin by SE-HPLC at 50° C. at 0 D, 3 D, 7 D & 13 D.

DESCRIPTION OF THE INVENTION

The erythropoietin used in the present invention is a recombinant human erythropoietin (rHu EPO). It is a 165 amino acid containing glycoprotein produced through recombinant DNA technology in animal cell lines such as Chinese Hamster Ovary (CHO) and Baby Hamster Kidney (BHK) cell lines. The recombinant human erythropoietin (rHu EPO) has the same biological properties as endogenous erythropoietin secreted in humans. It has a molecular weight of about 36,000 daltons with carbohydrate moiety composing about 30% of molecular weight.

Conjugated Erythropoietins are recombinant erythropoietin molecule covalently attached to a polyethylene glycol molecule. In preferred embodiments, the conjugated erythropoietin of the present invention comprises recombinant erythropoietin as defined by determination of a consensus sequence of naturally occurring erythropoietins being covalently linked to polyethylene glycol with a linker of the formulation selected from the group consisting of —CO—$(CH_2)_5$—$(OCH2CH2)$m-OR, —OCO—$(OCH2CH2)$n-OR and monomethoxy-PEG-Nitro phenyl carbamate/carbonate with the carbonyl of each polyethylene group forming an amide bond with one of said amino groups.

The present invention provides a stabilized pharmaceutical formulation of conjugated protein along with pharmaceutically acceptable carriers.

The present invention relates to a stabilized pharmaceutical composition comprising a conjugated erythropoietin, buffer, sugar, tonicity modifier and amino acid as an aggregation inhibitor at a pH range of 4.9 to 5.3.

The buffer is used in the present invention to maintain the pH in the range of about 4.8 to 5.5, preferably in the range of 4.9 to 5.4, more preferably in the range of 5.0-5.4 and most preferably at about pH 5.2-5.4 and the buffer is selected from the group consisting of acetate, arginine, succinate and histidine either alone or a combination thereof.

The polyol or sugar used in the present invention is selected from the group consisting of monosaccharide such as glucose and mannose, and the like either alone or in combination thereof, dissacharides such as sucrose, trehalose, and maltose, and the like either alone or in combination thereof, sugar alcohols such as mannitol and xylitol, and the like either alone or in combination thereof. More preferably the polyol or sugar used in the present invention is sucrose. The presence of sugars and sugar alcohols protect the molecules during storage at relatively high temperature.

Aggregation inhibitors reduce a polypeptide's tendency to form aggregates. The amino acids like arginine, glycine, methionine and lysine tend to reduce aggregation of the conjugated erythropoietin in a formulation for prolonged period of time.

A tonicity modifier is understood to be a molecule that contributes to the osmolality of a solution. The osmolality of a pharmaceutical composition is preferably regulated in order to maximize the active ingredient's stability and also to minimize discomfort to the patient upon administration. Examples of tonicity modifiers suitable for modifying osmolality include, but are not limited to sodium chloride, potassium chloride, calcium chloride and the like.

The novel, thermostable, aqueous pharmaceutical composition of recombinant conjugated erythropoietin described in the present invention has the following advantages:

1. Involves use of an aggregation inhibitor, which prevents the aggregation of the conjugated erythropoietin.
2. Involves use of a buffer system selected from the group consisting of acetate, arginine, succinate and histidine either alone or a combination thereof which maintains the pH of the formulation between 4.9 to 5.3 and also maintains the purity of the formulation at elevated temperature during storage.
3. Involves use of a sugar which provides better stability.
4. The pharmaceutical composition of present invention is maintained at pH between 4.9 to 5.3 which is critical in maintaining the purity and stability of the aqueous composition at elevated temperatures during storage.
5. Involves operational simplicity.

The following example illustrate the pharmaceutical compositions described in the present invention and the means of carrying out the invention to obtain a stabilized pharmaceutical composition comprising conjugated erythropoietin.

EXAMPLE 1 a) Screening and Selection of Aggregation Inhibitors

TABLE 1

Optimization of Arginine concentration

| S. No. | Excipients | Formulation 1 | Formulation 2 |
|---|---|---|---|
| 1 | Acetic Acid | 2.85 mg/ml | 3.5 mg/ml |
| 2 | Sucrose | 30 mg/ml | 30 mg/ml |
| 3 | Arginine | 8.5 mg/ml | 5.3 mg/ml |
| 4 | NaCl | 2.9 mg/ml | 2.9 mg/ml |
| 5 | Water for injection | q.s. to 1.0 ml | q.s. to 1.0 ml |

Experiment Details:
Formulation with varying amount of Arginine is prepared and charged at 50° C. Sample were withdrawn at different time point and checked for Purity by SE HPLC (High molecular weight impurity)

Results:
Result of above experiment (FIG. 1) shows that the formulation 1 which contain more Arginine (8.5 mg/ml) is shows more purity (Less aggregation) than the formulation 2 which contain less Arginine (5.3 mg/ml). Innovator formulation doesn't have Arginine. FIG. 1 clearly shows the less purity in RMP than the formulation 1 and 2 which are having Arginine in the formulation.

Conclusion:
Arginine in the formulation of Pegylated erythropoietin prevent the aggregation.

EXAMPLE 2 a) Screening of Buffers

In order to identify the buffer component, combinations were studied with various buffer components which included Histidine- HCl, Histidine- Acetate, Arginine-Acetate and Succinate. Detail composition of buffer is given in the Table: 2. PEG-EPO in different buffers were incubated at 40° C. for 2 days and then the result of reducing & non-reducing gels were compared with each other and with their respective controls, kept at 2-8° C.

TABLE 2

| Histidine- Hcl | Histidine- Acetate | Arginine- acetate | Succinate |
|---|---|---|---|
| 50 mM Histidine-Hcl | 50 mM Histidine-Acetate | 50 mM Arginine-acetate | 50 mM Succinate |
| 30 mg/ml Mannitol | 30 mg/ml Mannitol | 30 mg/ml Mannitol | 30 mg/ml Mannitol |
| 10 mM Methionine | 10 mM Methionine | 10 mM Methionine | 10 mM Methionine |
| 0.01% Pluronic F68 | 0.01% Pluronic F68 | 0.01% Pluronic F68 | 0.01% Pluronic F68 |

Results:
The observed depegylation of PEG-EPO from the above results is in the sequence of Histidine Acetate>Histidine Hcl>Arginine-acetate>Succinate buffer. (FIG. 2 & FIG. 3) It is also clear that the LMw (less Mw than EPO) impurity is also less in Succinate buffer in comparison to others. So, it can be said that PEG-EPO is more stable in Succinate buffer in comparison to other buffers. Moreover, arginine—acetate combination also showed less impurity and almost equal impurity formation as succinate buffer.

b) Further the Succinate and Acetate buffer were compared.
Detail composition of buffer is given in the Table: 3. PEG-EPO in Acetate and succinate buffers were incubated at 50° C. for 6 days and then the purity by SEC HPLC were compared:

Experiment Details:

TABLE 3

| | PEG-EPO in Acetate and succinate buffers | | | | |
|---|---|---|---|---|---|
| Sr. No. | Components | F1 | F2 | F3 | F4 |
| 1 | Acetic Acid | 15 mM | 30 mM | 0.5 µl/ml | 0.27 µl/ml |
| 2 | Succinic acid | 15 mM | — | — | — |
| 3 | Sucrose | 30 mg/ml | 30 mg/ml | — | — |
| 4 | Arginine | 25 mM | 25 mM | — | — |
| 5 | Methionine | — | — | 0.5 mg/ml | — |
| 6 | Glycine | — | — | 7.5 mg/ml | 7.5 mg/ml |
| 7 | Trehalose | — | — | 30 mg/ml | 30 mg/ml |

Results:

From the result of above experiment (FIG. 4) it can be observed that the formulation 2 (F2) having acetate buffer shows more purity compared the other formulation.

EXAMPLE 3 a) Effect of pH

Experiment Details:

Sample were prepared in the final composition having Acetate buffer, Arginine, sucrose and sodium chloride at different pH and charged at elevated temperature (40° C.) for pH dependent stability. Samples were analyzed by SE HPLC to determine the aggregation level at different pH;

TABLE 4 pH study

| Sr. No | Name of the ingredient | Formulation 1 | Formulation 2 | Formulation 3 | Formulation 4 | Formulation 5 |
|---|---|---|---|---|---|---|
| 1 | Peg EPO | 1.33 mg | 1.33 mg | 1.33 mg | 1.33 mg | 1.33 mg |
| 2 | Glacial Acetic Acid | 3.8 mg | 3.8 mg | 3.8 mg | 3.8 mg | 3.8 mg |
| 3 | Arginine | 8.5 mg | 8.5 mg | 8.5 mg | 8.5 mg | 8.5 mg |
| 4 | Sodium Chloride | 2.9 mg | 2.9 mg | 2.9 mg | 2.9 mg | 2.9 mg |
| 5 | Sucrose | 30.0 mg | 30.0 mg | 30.0 mg | 30.0 mg | 30.0 mg |
| 6 | Water for injection | q.s. to 1.0 ml | q.s. to 1.0 ml | q.s. to 1.0 ml | q.s. to 1.0 ml | q.s. to 1.0 ml |
|  | pH | 4.6 | 4.8 | 5.1 | 5.3 | 5.5 |

Results:

TABLE 5

Results of pH study

| | High molecular weight (H.M.W.) Impurities pH | | | | |
|---|---|---|---|---|---|
| Time points | 4.6 H.M.W | 4.8 H.M.W | 5.1 H.M.W | 5.3 H.M.W | 5.5 H.M.W |
| 0 D | 0.98 | 0.79 | 0.78 | 0.69 | |
| 15 D | 45.83 | 28.72 | 6.168 | 2.702 | 0.53 |

Conclusion:

Above results (Table 5 & FIG. 5) shows that by lowering the pH aggregation level (HMW) increases. Samples having pH 5.3 and 5.5 showed less aggregation level are found to be more stable as compared to lower pH samples.

EXAMPLE 4 a) Preparation of Conjugated Erythropoietin Composition

TABLE 6

Formulation details

| Sr. No | Name of the ingredient | Qty./ml |
|---|---|---|
| 1 | Peg EPO | 50 mcg-1.6 mg |
| 2 | Acetate buffer | 3.8 mg |
| 3 | Arginine | 8.5 mg |
| 4 | Sodium Chloride | 2.9 mg |
| 5 | Sucrose | 30.0 mg |
| 6 | Water for injection | q.s. to 1.0 ml |
|  | pH | 4.9 to 5.3 |

The novel formulations of conjugated erythropoietin are prepared using suitable combination of buffer, an aggregation inhibitor, tonicity modifier and stabilizer in suitable combination thereof.

Method of Preparation:

The process starts with the preparation of formulation buffer by dissolving Glacial acetic acid, Arginine, Sodium Chloride and Sucrose in water for injection in sequential manner by continues stirring at 500 rpm. pH is checked and, if required, the adjustment is made with glacial acetic acid solution (10%) or Sodium Hydroxide solution (0.1 N) to obtain the pH of 5.1±0.2. Make the volume 100% with WFI and stir the solution for homogeneity. Samples are withdrawn at this stage for IPQC tests.

Required amounts of formulation buffer and calculated amount of Peg-EPO Drug Substance is added with continuous stirring. Samples are withdrawn at this stage for IPQC tests. Filter the solution through 0.2 μm filter, using platinum cured silicon tubing Fill the solution in USP Type I glass PFS/vial and seal the container using sterile rubber stopper.

The novel formulation prepared by the said invention comprises an effective amount of biologically active conjugated erythropoietin which can be used in treating anemia associated with chronic renal failure. They are preferably used as injectable aqueous solutions.

EXAMPLE 5 a) Stability Study at −20° C.: for 24 Months

Method of Preparation:

Pegylated Erythropoietin was formulated at the protein concentration of 1.6 mg/mL in acetate buffer, the pH of the formulation was kept between 4.9-5.3. Formulated solution were filtered and filled in PETG bottle. The quantitative composition is given in the below Table 77.

TABLE 7

Formulation composition for Pegylated Erythropoietin

| Sr. No. | Ingredients | Quantity (mg/mL) |
|---|---|---|
| 1 | Peg EPO | 1.6 |
| 2 | Glacial acetic acid | 3.8 |
| 3 | Arginine | 8.5 |
| 4 | Sodium Chloride | 2.9 |
| 5 | Sucrose | 30.0 |
| 6 | Water for injection | q.s. to 1 mL |
| 7 | pH | q.s. to pH 4.9-5.3 |

Three batches of Pegylated Erythropoietin (1.6 mg/mL in PETG bottle) were charged at −20° C. for 24 months and were tested for the tests mentioned in Table 8.

TABLE 8

Tests to be performed for Pegylated Erythropoietin (1.6 mg/mL in PETG bottle) charged at −20° C.

| Sr. No. | Tests |
|---|---|
| 1 | pH |
| 2 | Protein conc. (mg/mL) |
| 3 | Relative potency (In vitro bioassay) |
| 4 | SE-HPLC (% purity) |

Data for the same are mentioned in the Table 9.

TABLE 9

Stability data for Pegylated Erythropoietin (1.6 mg/mL in PETG bottle) charged at −20° C.

| | −20° C. | | | | | | | | |
|---|---|---|---|---|---|---|---|---|---|
| | Batch 1 | | | Batch 2 | | | Batch 3 | | |
| Test | Initial | 12M | 24M | Initial | 12M | 24M | Initial | 12M | 24M |
| pH | 5.1 | 5.2 | 5.3 | 5.1 | 5.2 | 5.2 | 4.9 | 5 | 4.9 |
| Protein conc. (mg/mL) | 1.64 | 1.67 | 1.53 | 1.52 | 1.59 | 1.64 | 1.53 | 1.67 | 1.7 |
| Relative potency (In vitro bioassay) | 101 | 117 | 93 | 116 | 112 | 116 | 115 | 111 | 113 |
| SE-HPLC (% purity) | 99.1 | 99.3 | 98.9 | 99.8 | 99.7 | 99.7 | 99.5 | 99.6 | 99.6 |

Conclusion:
No significant change was observed in the pH of the protein up to 24 months at −20° C.
Protein concentration was monitored and no major change was observed in the protein concentration.
Relative potency was monitored using in-vitro bioassay method and found to be maintained up to 24 months.
SE-HPLC was used to monitor high molecular weight and low molecular weight impurities. As Pegylated Erythropoietin is a pegylated protein, it is critical to monitor the depegylation and aggregation during the course of time.
It can be observed from the data that the formulation composition is able to prevent aggregation and depegylation up to 24 months at −20° C. The formulation composition of Pegylated Erythropoietin is able to protect the protein against freeze denaturation.

b) Stability Study at 5° C.: for 24 Months
Method of preparation:
Pegylated Erythropoietin was formulated at the protein concentration of 1.33 mg/mL and 0.17 mg/mL in acetate buffer at pH 4.9-5.3. Formulated solution was filtered with 0.2 micron filter and filled in 1 mL USP type-I glass PFS. The quantitative composition is given in the Table.

TABLE 10

Formulation composition for Pegylated Erythropoietin

| Sr. No. | Ingredients | Quantity (mg/mL) |
|---|---|---|
| 1 | Peg EPO | 1.33-0.17 |
| 2 | Glacial acetic acid | 3.8 |
| 3 | Arginine | 8.5 |
| 4 | Sodium Chloride | 2.9 |
| 5 | Sucrose | 30.0 |

TABLE 10-continued

Formulation composition for Pegylated Erythropoietin

| Sr. No. | Ingredients | Quantity (mg/mL) |
|---|---|---|
| 6 | Water for injection | q.s. to 1 mL |
| 7 | pH | q.s. to pH 4.9-5.3 |

1) Three batches of Pegylated Erythropoietin (1.33 mg/mL in 1 mL USP type-I glass syringe barrel) was charged at 5° C. for 24 months and were tested for tests mentioned in Table 11.

TABLE 11

Tests to be performed for Pegylated Erythropoietin (1.33 mg/mL in 1 mL USP type-I glass PFS) charged at 5° C.

| Sr. No. | Tests |
|---|---|
| 1 | pH |
| 2 | Relative potency (In vitro bioassay) |
| 3 | SE-HPLC (% purity) |

Data for all the three batches are mentioned in Table 12

TABLE 12

Stability data for Pegylated Erythropoietin (1.33 mg/mL in 1 mL USP type-I glass syringe barrel) charged at 5° C.

| | 5° C. | | | | | | | | |
|---|---|---|---|---|---|---|---|---|---|
| | Batch 1 | | | Batch 2 | | | Batch 3 | | |
| Test | Initial | 12M | 24M | Initial | 12M | 24M | Initial | 12M | 24M |
| pH | 5.2 | 5.2 | 5.2 | 5.2 | 5.2 | 5.2 | 5.2 | 5.2 | 5.2 |
| Relative potency (In vitro bioassay) | 91 | 110 | 118 | 101 | 114 | 118 | 103 | 110 | 114 |
| SE-HPLC (% purity) | 99.0 | 98.2 | 98.2 | 99.1 | 98.3 | 98.3 | 99.2 | 98.7 | 98.2 |

Conclusion:
No change was observed in the pH of the protein up to 24 months at 5° C.
Relative potency was also found to be maintained up to 24 months.
It can be observed from the SE-HPLC data that there was no significant change in the purity of the protein up to 24 months at 5° C.

Data shows that formulation composition is able to maintain the pH of the protein and prevent aggregation up to 24 months at 5° C.

2) Three batches of Pegylated Erythropoietin (0.17 mg/mL in 1 mL USP type-I glass syringe barrel) was charged at 5° C. for 24 months and were tested for the tests mentioned in Table 13.

TABLE 13

Tests to be performed for Pegylated Erythropoietin (0.17 mg/mL in 1 mL USP type-I glass syringe barrel) charged at 5° C.

| Sr. No. | Tests |
|---|---|
| 1 | pH |
| 2 | Relative potency (In vitro bioassay) |
| 3 | SE-HPLC (% purity) |

Data for all the three batches are mentioned in Table 4.

TABLE 14

Stability data for Pegylated Erythropoietin (0.17 mg/mL in 1 mL USP type-I glass syringe barrel) charged at 5° C.

| | 5° C. | | | | | | | | |
|---|---|---|---|---|---|---|---|---|---|
| | Batch 1 | | | Batch 2 | | | Batch 3 | | |
| Test | Initial | 12M | 24M | Initial | 12M | 24M | Initial | 12M | 24M |
| pH | 5.0 | 5.1 | 5.1 | 5.0 | 5.1 | 5.1 | 5.0 | 5.0 | 5.1 |
| Relative potency (In vitro bioassay) | 112 | 113 | 108 | 105 | 92 | 97 | 114 | 96 | 104 |
| SE-HPLC (% purity) | 99.4 | 99.1 | 98.9 | 99.2 | 99.9 | 98.6 | 99.4 | 99.3 | 99.1 |

Conclusion:
No change was observed in the pH of the protein up to 24 months at 5° C.

Relative potency was also found to be maintained up to 24 months.

It can be observed from the SE-HPLC data that there was no significant change in the purity of the protein up to 24 months at 5° C.

Data shows that formulation composition is able to maintain the pH of the protein and prevent aggregation up to 24 months at 5° C.

c) Accelerated Stability Study at 25° C. : for 6 Months

1) Three batches of Pegylated Erythropoietin (1.33 mg/mL in 1 mL USP type-I glass syringe barrel) was charged at 25° C. for 6 months.

Data for all the three batches are mentioned in Table 15.

TABLE 15

Stability data for Pegylated Erythropoietin (1.33 mg/mL in 1 mL USP type-I glass syringe barrel) charged at 25° C.

| | 25° C. | | | | | |
|---|---|---|---|---|---|---|
| | Batch 1 | | Batch 2 | | Batch 3 | |
| Test | Initial | 6M | Initial | 6M | Initial | 6M |
| pH | 5.2 | 5.1 | 5.2 | 5.1 | 5.2 | 5.1 |
| Relative potency (In vitro bioassay) | 91 | 114 | 101 | 99 | 103 | 114 |
| SE-HPLC (% purity) | 99.0 | 94.4 | 99.1 | 94.4 | 99.2 | 93.8 |

Conclusion:
No significant change was observed in the pH of the protein up to 6 months at 25° C.

Relative potency was also found to be maintained up to 6 months.

Purity by SE-HPLC was around 94% in all three batches up to 6 months at 25° C.

2) Three batches of Pegylated Erythropoietin (0.17 mg/mL in 1 mL USP type-I glass syringe barrel) was charged at 25° C. for 6 months and were tested for the tests mentioned in 3) Table 16.

TABLE 16

Tests to be performed for Pegylated Erythropoietin (0.17 mg/mL in 1 mL USP type-I glass syringe barrel) charged at 25° C.

| Sr. No. | Tests |
|---|---|
| 1 | Relative potency (In vitro bioassay) |
| 2 | SE-HPLC (% purity) |

Data for all the three batches are mentioned in Table 27.

TABLE 27

Stability data for Pegylated Erythropoietin (0.17 mg/mL in 1 mL USP type-I glass syringe barrel) charged at 25° C.

| | 25° C. | | | | | |
|---|---|---|---|---|---|---|
| | Batch 1 | | Batch 2 | | Batch 3 | |
| Test | Initial | 6M | Initial | 6M | Initial | 6M |
| Relative potency (In vitro bioassay) | 112 | 107 | 105 | 96 | 114 | 112 |
| SE-HPLC (% purity) | 99.4 | 98.5 | 99.2 | 98.9 | 99.4 | 98.1 |

Conclusion:
Relative potency was found to be maintained up to 6 months.

It can be observed from the SE-HPLC data that there was no significant change in the purity of the protein up to 6 months at 25° C.

d) Stability Test of Conjugated Erythropoietin at 40° C.

SEC HPLC

TABLE 18

Results of stability study at 40° C.

| SE-HPLC | Total Purity |
|---|---|
| 1 D | 98.77% |
| 3 D | 97.85% |
| 7 D | 96.45% |
| 15 D | 91.89% |

Results:
Above results (Table 18 & FIG. 16) shows that formulation is stable at 40° C. for 15 days.

Western Blot:

In the western blot analysis: No single high molecular weight impurity band observed to be more intense than 2.0% of the principal band of reference standard. (FIG. 17 & FIG. 18)

e) Stability Test of Conjugated Erythropoietin at 50° C.
Purity Analysis by SEC HPLC

TABLE 19

Results of stability study at 50° C.

| Time point | Purity by SEC |
|---|---|
| 0 day | 98.3% |
| 50° C., 3 days | 98.0% |
| 50° C., 7 days | 97.4% |
| 50° C., 13 days | 94.4% |

Results:

Above result (FIG. 19) shows that formulation remains stable at 50° C. for 13 days. No significant increase in aggregation and low molecular weight impurity found.

We claim:

1. A liquid pharmaceutical formulation of PEG-EPO comprising:
   3.8 mg/mL acetate as buffer;
   8.5 mg/mL arginine as aggregation inhibitor;
   2.9 mg/mL sodium chloride and
   30.0 mg/mL sucrose at pH 4.9-5.3,
   wherein PEG-EPO is present at a concentration of 0.05 mg/mL to 1.6 mg/mL.

2. A liquid pharmaceutical composition comprising a syringe pre-filled with the liquid pharmaceutical formulation as claimed in claim 1.

* * * * *